US00PP09126P

United States Patent [19]

Glicenstein

[11] Patent Number: Plant 9,126

[45] Date of Patent: May 2, 1995

[54] CHRYSANTHEMUM PLANT NAMED WARM MEGAN

[75] Inventor: Leon Glicenstein, Salinas, Calif.

[73] Assignee: Yoder Brothers, Inc., Barberton, Ohio

[21] Appl. No.: 155,238

[22] Filed: Nov. 22, 1993

[51] Int. Cl.[6] ..... A01H 5/00

[52] U.S. Cl. ..... Plt./82.3

[58] Field of Search ..... Plt. 82.3, 74.1, 76, Plt. 79

[56] References Cited

U.S. PATENT DOCUMENTS 4,616,099 10/1986 Sparkes ..... 47/58

OTHER PUBLICATIONS

Broertjes, et al., 1980, "A mutant of a mutant of a . . . Irradiation of progressive radiation-induced mutants in a mutation breeding programme with *Chrysanthemum morifolium*", Euphytica, 29:526–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by X-rays", Am. Soc. Hort. Sci. Proc., pp. 613–620.

Broertjes, 1966, "Mutation breeding of chrysanthemums", Euphytica, 15:156–162.

Dowrick, et al., 1966, "The induction of mutations in Chrysanthemum using X- and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Warm Megan particularly characterized by its flat capitulum form; decorative capitulum type with many disc florets in natural season fall flowerings, to daisy capitulum type with many ray florets in spring flowerings; warm orange-bronze ray floret color; diameter across face of capitulum of 45 to 54 mm when fully opened; branching pattern is spreading and prolific, with 6 to 9 breaks after pinch when grown outside under natural daylength in fall flowerings and in 10 cm pots for spring flowerings; natural season flower date of August 23 to 29 when planting rooted cuttings on June 21 to June 23 in Salinas, Calif., and September 27 to October 5 when planting rooted cuttings June 15 to June 18 in Hightstown, New Jersey; flowering response of 48 to 49 days after rooting in no light/no shade program sin spring; plant height of 30 to 36 cm when grown in fall under natural daylength with no growth regulators in N.J., and 15 to 25 cm when grown in 10 cm pots in spring with 0 to 1 application of 2500 ppm B-9 SP; and durable, uniform performance.

1 Drawing Sheet

The present invention comprises a new and distinct cultivar of Chrysanthemum, botanically known as *Dendranthema grandiflora,* and referred to by the cultivar name Warm Megan.

Warm Megan, identified as 8147 (85-125B02), is a product of a mutation induction program. The new cultivar was discovered and selected by Leon Glicenstein on Jul. 8, 1991, in a controlled environment in Salinas, Calif. as one flowering plant within a flowering block established as rooted cuttings from stock plants which had been exposed as unrooted cuttings to an X-ray source of 2000 rads in Fort Myers, Fla. on Mar. 6, 1991. The irradiated patent cultivar was the cultivar identified as Megan, disclosed in plant patent application Ser. No. 07/822,700 now U.S. Plant Pat. No. 8,756, a garden mum with a decorative flower with many disc florets in the fall, to a daisy with many ray florets in the spring, with a red-purple flower color.

The irradiation program resulting in Warm Megan has as its primary objective the expansion of color ranges of the parent cultivar Megan. The irradiation program comprised irradiating cuttings of the parent cultivar at irradiation levels of 1500, 1750 and 2000 rads. A total of 2167 cuttings harvested from a total of 225 irradiated plants were planted on May 13, 1991, May 6, 1991 and May 6, 1991, respectively. Of these, 44 initial selections were made, which selections were then revegetated and reflowered. Three consecutive flowerings resulted in discarding 38 of the original 44 selections on Mar. 19, 1992. One code was reselected, which reselection was ultimately discarded on Nov. 10, 1992. The remaining six selections were maintained as PIs (Possible Introductions) and further trialed in Salinas, Calif., Highstown, N.J. and Leamington, Ontario, Canada, ultimately resulting in the decision to discard five of these codes on Oct. 1, 1992 and to introduce selection 8147 as Warm Megan.

The first act of asexual reproduction of Warm Megan was accomplished when vegetative cuttings were taken from the initial selection in September 1991 in a controlled environment in Salinas, Calif., by technicians working under supervision of Leon Glicenstein.

Horticultural examination of controlled flowerings of successive plantings has shown that the unique combination of characteristics as herein disclosed for Warm Megan are firmly fixed and are retained through successive generations of asexual reproduction.

Warm Megan has not been observed under all possible environmental conditions. The phenotype may vary significantly with variations in environment such as temperature, light intensity and daylength, without, however, any variation in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Warm Megan, which, in combination, distinguish this Chrysanthemum as a new and distinct cultivar:

1. Flat capitulum form.
2. Decorative capitulum type with many disc florets in natural season fall flowerings compared to typical decorative type cultivars to daisy capitulum type with many ray florets in spring flowerings.
3. Warm orange-bronze ray floret color.
4. Diameter across face of capitulum of 45 to 54 mm when fully open.
5. Branching pattern is spreading and prolific, with 6 to 9 breaks after pinch when grown outside under natural daylength in fall flowerings and in 10 cm pots for spring flowerings.
6. Natural season flower date of August 23 to 29 when planting rooted cuttings on June 21 to June 23 in Salinas, Calif., and September 27 to October 5 when planting rooted cuttings June 15 to June 18 in Hightstown, N.J.
7. Flowering response of 48 to 49 days after rooting in no light/no shade programs in spring.
8. Plant height of 30 to 36 cm when grown in fall under natural daylength with no growth regulators in New Jersey, and 15 to 25 when grown in 10 cm pots in spring with 0 to 1 application of 2500 ppm B-9 SP.
9. Plants within the same plot flower uniformly, and the flowers are long lasting.

The accompanying photographic drawing is a color photograph of Warm Megan grown as a pinched garden mum under natural season outside conditions in Salinas, Calif., with the colors being as nearly true as possible with illustrations of this type. Plants were grown outside and dug and transplanted into 15 cm bulb pans at flowering time for photography purposes.

Of the commercial cultivars known to the inventor, the most similar in comparison to Warm Megan is the parent cultivar Megan. All traits of Megan are similar to those of Megan, except for the ray floret color. The ray floret color of Warm Megan is warm orange-bronze, while the ray floret color of Megan is described as red-purple.

In the following description, color references are made to The Royal Horticultural Society Colour Chart. The color values were determined on plant material grown as a pinched garden mum grown under natural season outside conditions in Salinas, Calif. on Aug. 27, 1993.

Classification:

*Botanical.*—*Dendranthema grandiflora* cv Warm Megan.

*Commercial.*—Flat decorative spray pot mum and garden mum with many disc florets in the fall, to flat daisy spray pot mum and garden mum with many ray florets in the spring.

INFLORESCENCE

A. Capitulum:

*Form.*—Flat.

*Type.*—Flat decorative spray pot mum and garden mum with many disc florets in the fall, to flat daisy spray pot mum and garden mum with many ray florets in the spring.

*Diameter across face.*—45 to 54 mm when fully opened.

B. Corolla of ray florets:

*Color (general tonality from a distance of three meters).*—Warm orange-bronze.

*Color (upper surface).*—Fully mature petal tips closest to 171B. Immature petals 171A to 171B, slightly tinged with 179B.

*Color (under surface).*—171C, slightly tinged with 179B.

*Shape.*—Flat straight. Cross section of inner, immature ray florets concave.

C. Corolla of disc florets:

*Color (mature).*—14B.

*Color (immature).*—14B, slightly tinged with 144B.

D. Reproductive organs:

*Androceium.*—Present on disc florets only, moderate pollen

*Gynoecium.*—Present on both ray and disc florets.

PLANT

A. General appearance:

*Height.*—30 to 36 cm when grown in fall under natural daylength with no growth regulators in New Jersey and 15 to 25 cm when grown in 10 cm pots in spring with 0 to 1 applications of 2500 ppm B-9 SP.

*Branching pattern.*—Spreading and prolific, with 6 to 9 breaks after pinch when grown outside under natural daylength in fall flowerings and in 10 cm pots for spring flowerings.

B. Foliage:

*Color (upper surface).*—147A.

*Color (under surface).*—147B.

*Shape.*—Relatively small, shallow lobes, and slightly serrated.

I claim.

1. A new and distinct Chrysanthemum plant named Warm Megan, as described and illustrated.

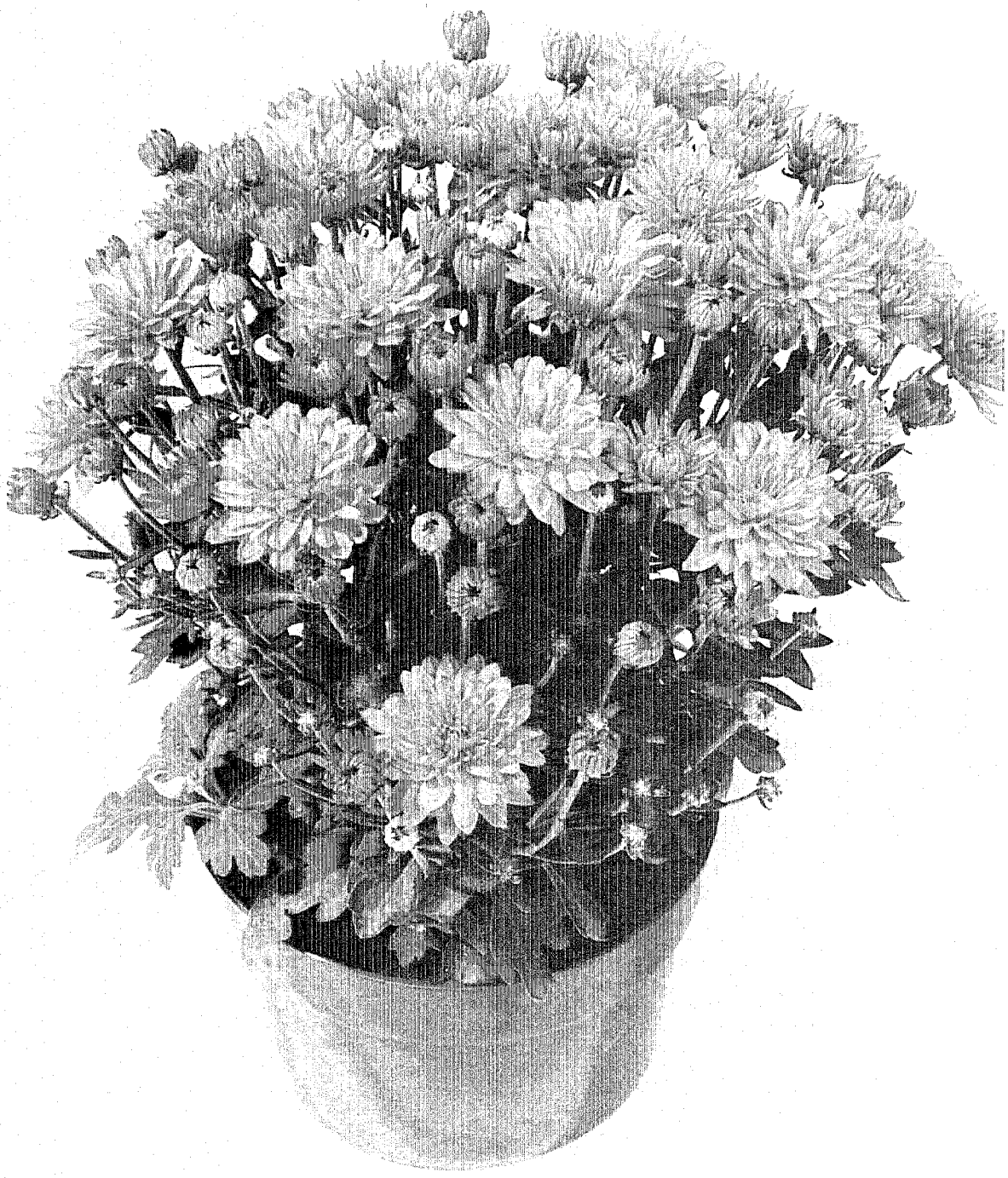

* * * * *